US008273863B1

(12) United States Patent
Jordan

(10) Patent No.: US 8,273,863 B1
(45) Date of Patent: Sep. 25, 2012

(54) NUCLEIC ACID LADDERS

(75) Inventor: Heather J. Jordan, Gaithersburg, MD (US)

(73) Assignee: Life Technologies Corporation, Carlsbad, CA (US)

(*) Notice: Subject to any disclaimer, the term of this patent is extended or adjusted under 35 U.S.C. 154(b) by 0 days.

(21) Appl. No.: 09/613,903

(22) Filed: Jul. 11, 2000

Related U.S. Application Data

(63) Continuation of application No. 08/892,884, filed on Jul. 15, 1997, now abandoned.

(51) Int. Cl.
*C07H 21/04* (2006.01)
*C12Q 1/68* (2006.01)

(52) U.S. Cl. .................................... 536/23.1; 435/6.1
(58) Field of Classification Search ............... 536/23.1; 435/4, 6; 204/456
See application file for complete search history.

(56) References Cited

U.S. PATENT DOCUMENTS

| | | | |
|---|---|---|---|
| 4,403,036 A | 9/1983 | Hartley et al. | |
| 4,415,732 A | 11/1983 | Caruthers et al. | 536/27 |
| 4,458,066 A | 7/1984 | Caruthers et al. | 536/27 |
| 4,500,707 A | 2/1985 | Caruthers et al. | 536/27 |
| 4,668,777 A | 5/1987 | Caruthers et al. | 536/27 |
| 4,900,659 A | 2/1990 | Lo et al. | 435/6 |
| 5,030,566 A | 7/1991 | Son et al. | 435/91 |
| 5,108,179 A | 4/1992 | Myers | 356/344 |
| 5,268,568 A * | 12/1993 | Lee | 250/214 B |
| 5,316,908 A * | 5/1994 | Carlson et al. | 435/6 |
| 5,527,670 A * | 6/1996 | Stanley | 435/6 |
| 5,635,365 A * | 6/1997 | Ansari et al. | 435/15 |
| 5,714,326 A | 2/1998 | Dawson | 435/6 |
| 5,792,664 A | 8/1998 | Chait et al. | 436/89 |
| 5,834,201 A * | 11/1998 | Hartley | 435/6 |
| 5,840,575 A * | 11/1998 | Hyman | 435/320.1 |
| 5,939,293 A | 8/1999 | Hyman | 435/91.5 |
| 7,132,520 B2 * | 11/2006 | Hartley | 536/22.1 |

FOREIGN PATENT DOCUMENTS

| | | |
|---|---|---|
| EP | 0 466 404 A1 | 1/1992 |
| JP | 63-113359 | 5/1988 |
| WO | WO 91/18095 | 11/1991 |
| WO | WO 93/14224 | 7/1993 |
| WO | WO 95/11971 | 5/1995 |

OTHER PUBLICATIONS

Invitrogen (Carlsbad, CA) 1997 Product Catalog, "1 kb ladder," p. 113.*
Novagen (Milwaukee, WI) 1997 Product Catalog, pp. 115-117.*
Life Technologies Product cvatalogue and reference Guide 1995-1996. 1995. pp. 14-2-14-5.*
Life Technologies Product Catalogue and Reference Guide 1995-1996, pp. 14-2-14-5.*
Merriam-Webster OnLine, Meriam-Webster Dictionary, accessed Nov. 30, 2003, "substantial.".*
Life Technologies Catalogue, 1995-1996.*
Stratagene Cloning Systems Catalogue, 1993, pp. 122 and 124.*
Schneeberger et al., "Quantitative detection of reverse transcriptase-PCR products by means of a novel and sensitive DNA stain," PCR Methods and Applications, 1995, 4(4), 234-238.*
Stratagene Cloning Systems Catalog, 1993, pp. T20-T23.*
Life technologies, "GIBCO BRL Product Catalogue and Reference Guide 1995-1996," pp. 14-2, 14-3, and 14-4.*
Bayou Biolabs (Harahan, LA) Products for Molecular Biology 1998 Catalog, "DNA Ladders," pp. 2-3.
Bernards, A. et al., "Pulsed field gradient electrophoresis of DNA digested in agarose allows the sizing of the large duplication unit of a surface antigen gene in trypanosomes," Chemical Abstracts 105:187, Abstract No. 92470r (1986).
Carman, W.F. and C. Williamson, "Detection of Enzymatically Amplified Human Immunodeficiency Virus DNA by Oligonucleotide Solution Hybridization and by Incorporation of Radiolabeled Deoxynucleotides," J. Clin. Microbiol. 27:2570-2573 (1989).
Gensura (Del Mar, CA) Winter 1997-98 Product Description, "Superladder-mid2 1 Kb ladder," three pages.
Gralla, J.D., "Rapid 'footprinting' on supercoiled DNA," Proc. Natl. Acad. Sci. USA 82:3078-3081 (1985).
Huang, J. et al., "Restriction endonuclease analysis of granulosis virus DNA of *Agrotis exclamationis* Linnaeus," Chemical Abstracts 107:175, Abstract No. 34093a (1987).
Jones, C.P. et al., "Separation of yeast chromosomes in the megabase range suitable as size markers for pulsed-field gel electrophoresis," Chemical Abstracts 112:172, Abstract No. 230760h (1990).
Life Technologies (Gaithersburg, MD) GIBCO BRL 1997/1998 Products and Reference Guide, "1 Kb DNA Ladder," p. 16-5.
Mathew, M.K. et al., "High-Resolution Separation and Accurate Size Determination in Pulsed-Field Gel Electrophoresis of DNA. 1. DNA Size Standards and the Effect of Agarose and Temperature," Biochemistry 27:9204-9210 (1988).
Minter, S. and P. Sealey, "Nucleic Acid Molecular Weight Markers," in: *Gel electrophoresis of nucleic acids: a practical approach*, Rickwood, D. and B.D. Hames, eds., IRL Press, Washington, D.C., pp. 227-232 (1982).
Pharmacia Biotech (Piscataway, NJ) 1997 Biodirectory Product Catalog, "KiloBase DNA Marker," p. 58.
Promega (Madison, WI) 1997 Biological Research Products Catalog, "1kb DNA Ladder," p. 17.
Sigma (St. Louis, MO) 1997 Biochemicals and Reagents for Life Science Research Catalog, "DNA Ladder, 1 kb," p. 1530.
Stratagene (La Jolla, CA) 1997/1998 Catalog, "Kb DNA Ladder," p. 130.
English language abstract of Japanese Patent No. 63-113359, WPI Accession No. 88-177809 (1988).
Novagen (Milwaukee, WI) 1997 Catalog, pp. 115-117 (1997).
NOVAGEN, , "pp. 4-5, 115-117", *Novagen 1997 Catalog* Published by Novagen, Milwaukee, WI 1997 , 4-5, 115-117.
EP 98934535, Supplementary European Search Report mailed Nov. 8, 2004.
PCT/US98/14569, International Search Report mailed Oct. 27, 1998.

* cited by examiner

*Primary Examiner* — Bradley L Sisson

(57) ABSTRACT

The present invention provides nucleic acid compositions or ladders which may be used as standards for estimating the size (in base pairs) and or mass of nucleic acid molecules of unknown size and/or mass. The invention also relates to methods for producing such compositions or ladders, ladders or compositions produced by such methods, and to methods for estimating the size and/or mass of nucleic acid molecules by comparison to these nucleic acid sizing ladders.

19 Claims, 2 Drawing Sheets

NUCLEIC ACID LADDERS

CROSS-REFERENCE TO RELATED APPLICATIONS

This application is a continuation of application Ser. No. 08/892,884, filed Jul. 15, 1997, now abandoned.

INTRODUCTION

A common method of analyzing nucleic acid (e.g., DNA or RNA) fragments is by separation in an agarose or polyacrylamide gel matrix. Such matrices provide a medium in which such fragments of different sizes and forms may be analyzed. In the presence of an electrical current, nucleic acid fragments will migrate through such a gel matrix in the direction of the positive electrode. Since small, linear molecules migrate more easily and quickly through the pores of a matrix than do larger molecules, the matrix acts as a molecular sieve, separating fragments of different sizes. Larger nucleic acid fragments are typically electrophoresed on low concentration agarose gels, while smaller fragments are separated on higher concentration agarose gels or on polyacrylamide gels, since polyacrylamide has a higher resolution capacity than agarose.

Detection of nucleic acid molecules electrophoresed in agarose or polyacrylamide gels can be accomplished by a variety of techniques, including the use of fluorescent dyes such as ethidium bromide and SYBR Green. These dyes bind to the nucleic acid molecules and fluoresce when exposed to ultra violet (UV) light. Alternatively, the nucleic acid molecules can be detected by chemically coupling them with radioactive, fluorescent or chemiluminescent labels.

Nucleic acid molecular weight standards are useful tools for estimating the quality, size, and/or quantity of the nucleic acid sample. A standard is typically fractionated simultaneously with the sample (e.g., in parallel with the sample), and following detection, a comparison is made between the sample band(s) and the bands of the standard. Knowing the size (in base pairs) of the standard allows the size of the unknown fragment(s) to be estimated.

Common standards used for estimating the size of nucleic acid fragments include restriction digests of nucleic acid molecules such as naturally occurring genomic DNA of bacteriophages (e.g., lambda bacteriophage) resulting in a population of nucleic acid fragments of known size. These types of standards are commonly called "nucleic acid markers" (e.g., "DNA markers").

Another type of nucleic acid standard is produced by engineering plasmids to contain restriction/cleavage sites for one or more specific restriction endonucleases at particular intervals in the plasmid. Upon digestion of the plasmid with the specific endonuclease(s), nucleic acid fragments of specific known sizes are generated. For accuracy in size determination and for ease of use, it is beneficial to have numerous bands that increase in size in regular, even intervals. These types of standards are commonly called "nucleic acid ladders" (e.g., "DNA ladders"). Preferably, each fragment generated from the digestion forms a discrete band and more preferably the bands from the digest are equivalent or substantially equivalent in intensity when stained to facilitate detection of each band.

None of the commercially available DNA ladders provide a range of standard fragment sizes wherein the electrophoretic bands of high molecular weight of 1 kilobase (kb) or larger and the low molecular weight bands of 1 kb or smaller, especially bands in the range of 100-500 bp, are sharply resolved and are equal or substantially equal in intensity so as to be able to size nucleic acid fragments of interest spanning a broad molecular weight range using one nucleic acid standard.

A 1 Kb DNA Ladder is currently available from Life Technologies, Inc. (Rockville, Md.). This ladder contains twelve bands in increments of 1018 bp, a 1636 bp band, a 517 bp band, and several smaller size bands ranging in size from 506 bp to 75 bp. However, the fragments smaller than 1 Kb appear less intense and less discrete than the 1018 bp increment bands. Also, the 1,636 bp band and the 517/506 bp doublet band stain more intensely than do other bands in the ladder.

Another commercially available product is the "Kb DNA Ladder", available from Stratagene (La Jolla, Calif.). This product contains twelve bands of exact 1 Kb increments and three bands smaller than 1 Kb. The intensity of the bands smaller than 2 Kb is about half that of the bands 2 Kb and larger. In addition, the ladder bands greater than 6 Kb stain with less intensity than the 2 Kb-6 Kb bands.

The Promega Corporation (Madison, Wis.) sells a 1 Kb DNA Ladder with eight 1 Kb increment bands ranging from 1 Kb to 10 Kb (there are no 7 or 9 Kb bands in this ladder) and three bands below 1 Kb. The 1 Kb and 3 Kb bands in the 1 Kb DNA Ladder available from Promega have increased intensity (>2-fold) to serve as reference points within the ladder. In addition to this, the 8 Kb and 10 Kb bands are significantly more intense than other bands in the ladder and the 0.25, 0.5, and 0.75 Kb bands are of various intensities.

The 1 Kb DNA Ladder sold by Sigma Chemical Company (St. Louis, Mo.) is virtually identical to the Promega product, except it only contains one band below 1 Kb (the 0.5 Kb band). Several of the bands in the 1 Kb DNA Ladder sold by Sigma vary in their intensities and this ladder contains only one band smaller than 1 Kb.

Pharmacia Biotech (Piscataway, N.J.) sells a product called "Kilobase DNA Marker" which is likely to be the same product described above and sold by Sigma.

A "1 Kilobase DNA Ladder" is sold by Bayou Biolabs (Harahan, La.) which has bands in 1 Kb increments up to 10 Kb. This product does not contain any bands smaller than 1 Kb. The Bayou Biolabs product has a triple-intense 5 Kb band and does not contain any bands smaller than 1 Kb.

Two other commercially available versions of a 1 Kb DNA Ladder, sold by GenSura (DelMar, Calif.) and Invitrogen (San Diego, Calif.) are believed to be identical. These ladders have 1 Kb increment bands from 1 Kb to 15 Kb and, as with the Bayou Biolabs product, have no bands smaller than 1 Kb and a triple-intense 5 Kb band.

Therefore, in view of the above, there is a need for a DNA ladder which spans a broad length range and which, when separated on a gel and stained, generates discrete bands which are clear and visible and are of relative equal intensity compared to each other. This is especially significant for band lengths smaller than 1 Kb (particularly those of 500 bp and smaller).

SUMMARY OF THE INVENTION

The present invention concerns a composition of matter comprising a number of different sized nucleic acid fragments (two or more) for use in estimating size of unknown nucleic acid fragments. Specifically, the present invention relates to nucleic acid ladders for estimating the size (in base pairs) of nucleic acid fragments spanning a broad range of molecular weight sizes. The nucleic acid compositions and ladders of the invention include RNA or DNA and may be single or double stranded, although double stranded DNA ladders are preferred. Specifically, the invention relates to nucleic acid ladders or compositions wherein all or substantially all of the bands are substantially equal in intensity and/or wherein all or substantially all of the bands are substantially equal in relative mass. In a preferred aspect of the invention, the compositions or ladders are comprised of nucleic acid fragments in increments of about 1 Kb (kilobase=1,000 bases or base pairs) (e.g., 1 Kb, 2 Kb, 3 Kb, 4 Kb, 5 Kb etc.) and one or more nucleic acid fragments smaller than 1 Kb (for example, in increments 10 bp, 20 bp, 30 bp, 40 bp, 50 bp, 60 bp, 70 bp, 80 bp, 90 bp 100 bp etc. or any combination thereof); wherein substantially all of the fragments of the ladder or composition are substantially equal in intensity when detected by staining, and/or wherein substantially all of the fragments are substantially equal in relative mass.

Preferably, the nucleic acid ladders and compositions of the invention have two or more bands (preferably four, five, six, seven, eight or more bands) ranging from about 25 Kb to about 100 bp or smaller, preferably 20 Kb to 100 bp, more preferably 15 Kb to 100 bp and most preferably 12 Kb to 100 bp, although smaller ranges are contemplated by the invention.

The nucleic acid ladders or compositions of the invention preferably contain a mixture of nucleic acid fragments of different lengths wherein the copy number of each fragment size is adjusted such that the relative mass of each fragment is substantially the same. By having substantially the same relative mass, the bands of the ladders or compositions of the invention have substantially equal intensity when staining after separation by gel electrophoresis. In another aspect, the fragments of the ladders or compositions are produced by cleavage of one or more nucleic acid molecules at one or more enzyme restriction enzyme sites. These molecules may comprise any vector including plasmids, cosmids, or phagemides.

More specifically, a ladder or compositions of the present invention is produced from a plasmid, designed to contain 9 copies of a 100 bp sequence, 4 copies of a 200 bp sequence, 3 copies of a 300 bp sequence, 2 copies of a 400 bp sequence, 2 copies of a 500 bp sequence, one copy each of a 650 bp, a 850 bp, and a 1650 bp sequence, and 12 copies of a 1000 bp sequence. A number of different sized fragments are present in multiple copies in the plasmid such that each fragment when generated by the appropriate endonuclease digestion has substantially the same relative mass as any other different sized fragment in the ladder or composition. Thus, the compositions or ladders of the invention comprise a number of different bands (each band representing a different sized fragment), wherein each band has substantially the same intensity after gel electrophoresis and staining. The fragments in this preferred aspect of the invention are prepared by digesting the plasmid with restriction endonucleases, thereby producing fragments ranging from about 12 kb to about 100 bp, which when stained, appear as distinct bands of substantially equal intensity after gel electrophoresis.

The present invention also provides nucleic acid ladders or compositions of the invention which comprise a mixture of nucleic acid fragments of different lengths. Each different sized fragment of the ladders or compositions of the invention may differ in size by X base pairs (bp), wherein X is an integer equal or greater than 10. Preferably, the relative mass of each different sized fragment is substantially equivalent such that discrete bands of substantially equal intensity are produced when the fragments are resolved on a gel and stained.

The invention also relates to a method for preparing the ladders or compositions of the invention. Such methods comprise providing sufficient numbers of copies of each fragment of a desired size such that the mass of each fragment is substantially equivalent. Generally, more copies of smaller fragments are needed to equalize the mass of a larger fragments. The multiple fragments for preparing the ladders or compositions of the invention may be provided separately or in a pre-mixed form. In any event, the separately provided fragments would be mixed prior to gel separation.

The methods of the invention also comprise:

(a) mixing one or more restriction enzymes with one or more nucleic acid molecules (preferably plasmids, cosmids, or phagemids); and (b) incubating the mixture under conditions favoring the cleavage of said nucleic acid molecules at one or more of the restriction sites, thus providing the ladders or compositions of the invention. Cleavage can be a partial digestion, a complete digestion, or a combination of both, depending upon the design of the nucleic acid molecule. Partial digestion generates a population of multimers (e.g. monomer repeat, dimer repeat, trimer repeat, tetramer repeat, etc.), thereby forming a ladder, while complete digestion generates distinct size bands (depending on the location of the restriction sites The invention also relates to methods for determining the size of a nucleic acid molecule, a preferred such method comprising:

(a) separating according to size the nucleic acid ladder or composition of the invention, and the nucleic acid molecule to be sized; and (b) determining the size of the nucleic acid molecule by comparison to the fragments or bands of the nucleic acid ladder or composition.

The invention further provides kits comprising a carrier means, such as a box, carton or the like, being compartmentalized to receive in close confinement therein one or more container means, such as tubes, vials, ampules, bottles, or the like, wherein a first container means comprises the nucleic acid ladder or composition of the present invention. The kit of the invention may comprise the composition or ladder in a single container (pre-mixed) or may comprise fragments of the ladder or composition in separate containers which may be mixed at a later time.

The invention also concerns nucleic acid molecules (DNA or RNA, preferably double stranded DNA) for preparing the ladders compositions (or fragments thereof) of the invention. Such molecules are preferably plasmids, cosmids, or phagemids. A preferred plasmid is pKB1847. Host cells containing such molecules are also contemplated by the invention.

BRIEF DESCRIPTION OF THE DRAWINGS

These and other features, aspects, and advantages of the present invention will become better understood with reference to the following description and appended claims, and accompanying drawings where:

DETAILED DESCRIPTION

Figure 1:
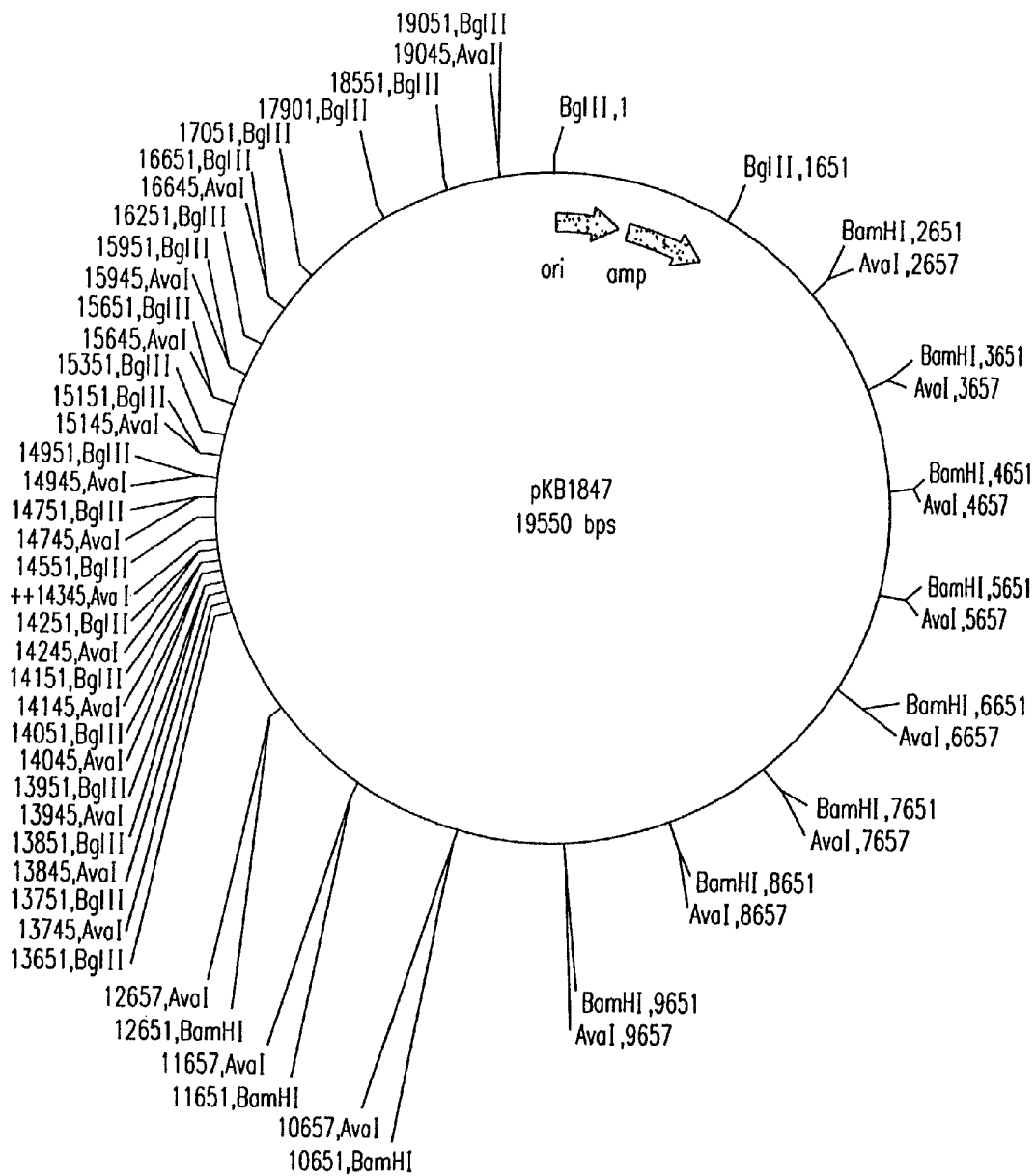
FIG. 1 shows a restriction map of plasmid pKB1847.

The present invention relates to nucleic acid molecules which may be used as standards for estimating the size (in base pairs) and/or mass of linear, double stranded or single stranded nucleic acid molecules separated by size, preferably by electrophoresis on agarose or polyacrylamide gels. The nucleic acid molecules of the invention may be DNA molecules, RNA molecules or DNA/RNA hybrid molecules, and may be double-stranded or single-stranded.

In a preferred embodiment of the invention, the nucleic acid molecules (or fragments of the ladders or compositions of the invention) are produced from one or more vectors (e.g., plasmids, cosmids, and phagemids) designed to contain copies of fragments of different lengths. However, any nucleic acid molecule or combination of molecules may be used to produce the ladders or compositions of the invention. Different sized fragments are then provided (as a premixture or separately for later mixing) such that the relative mass of each fragment length is substantially equivalent. Relative mass is defined as the ratio of each fragment mass compared to total mass of all fragments. Mass of a fragment is defined as the size (number of base pairs (bp)) of each fragment length multiplied by the number of copies of same fragment; for example, if a ladder or composition has three (3) different sized fragments (fragment 1, 100 bp at 50 copies; fragment 2, 500 bp at 10 copies; and fragment 3, 1000 bp at 5 copies) the mass of each fragment would be 5000 (e.g., 5 copies of a 1,000 bp fragment would have the mass of 5×1,000=5,000). The total mass would therefore be 15,000 (5,000+5,000+5,000=15,000). Relative mass (in percent) can be calculated by dividing the mass of a particular fragment over the total mass of all the fragments multiplied by 100. Thus, the relate mass of each fragment would be 33%. Relative mass is substantially equal when the relative mass of each fragment is no more than 3 times the relative mass of another fragment, preferably, no more than 2.5 times the relative mass of another fragment, more preferably 2 times the relative mass of another fragment, still more preferably 1.5 times the relative mass of another fragment, and most preferably each fragment has about the same relative mass.

For instance, in the preferred ladder of the invention, the relative mass of the 100 bp fragment can be calculated by dividing the mass of 100 bp fragment, 9 copies ×100 bp=900, over the total mass of the fragments in the ladder, 19,550 bp (see Table 1), multiplied by 100 results in a relative mass of 4.6%. In a second example, the 1,650 bp fragment (1,650×1 copy=1,650) divided by the total mass of the all the fragments of the ladder, 19,550, multiplied by 100 gives a relative mass of 8.4%. Therefore, since the relative mass of the 1,650 bp fragment is less than three times the relative mass of the 100 bp fragment, the relative mass of the fragments is considered to be substantially equal as defined herein.

According to this aspect of the invention, a particularly preferred nucleic acid molecule generates a 1 kb ladder (increments of about 1 Kb) and contains about 9 copies of a 100 bp sequence, 4 copies of a 200 bp sequence, 3 copies of a 300 bp sequence, 2 copies of a 400 bp sequence, 2 copies of a 500 bp sequence, one copy each of a 650 bp, a 850 bp sequence and a 1,650 bp sequence. The 1 kb ladder is generated by partial digestion of the vector containing 12 copies of about a 1 kb (1000 bp) sequence, while the multiple copies of fragments smaller than 1 kb are generated by complete digestion. Increasing the number of smaller sized fragments provides equalization of the relative mass of all fragments thereby allowing substantially equal band intensity.

As noted, one or more nucleic acid molecules may be used to prepare the ladder of composition of the invention. That is, one or a number of fragments can be made from one or more molecules, and the fragments can be isolated and maintained separately or premixed.

As will be understood by those of ordinary skill in the art, the nucleic acid molecules used to form the nucleic acid sizing ladder or composition of the invention are preferably linear or circular DNA molecules which are cleavable by a restriction enzyme. For example, the nucleic acid molecules may be derived from a chromosome, a vector, a cosmid, a plasmid or a viral genome. Preferably, the nucleic acid molecules are vector or viral molecules and derivatives thereof. The nucleic acids present in the vector or viral molecule may include exogenous nucleic acids which have been joined to produce the vector or viral molecule. In one preferred embodiment, the nucleic acid is DNA.

In order to prepare the multiple copies of the fragments of the invention, the method described in Example 1 can be used. Multiple fragments of a desired size can be cloned into a selected restriction site in a head to tail fashion so as to avoid hairpin formation. The vector containing the proper number of multiples desired so as to have substantially equal relative mass can be selected according to size. The multiples are preferably flanked with one or more unique restriction endonuclease sites so that they may be removed from one vector and inserted in another vector as a "cassette". This allows the preparation of a single vector which contains the multiple fragments to make the ladder or composition of the invention. This vector can then be used, by digesting with the appropriate endonucleases under the appropriate conditions, to prepare the ladders or compositions of the invention. Alternatively, the different sized fragments (or multiples thereof) may be inserted into separate vectors, the fragments can be isolated and then premixed or stored for later mixing to make the ladders or compositions of the invention. These fragments would be mixed in appropriate amounts to provide a ladder or composition, wherein each fragment of the ladder or composition has substantially the same relative mass. The above method can be repeated for any size fragment multiples, and the multiples combined as desired. Restriction sites which allow head-to-tail ligation of fragments are asymmetrical restriction sites known to those in the art and include, for example, AvaI and BanII.

Where the multiple copies of the fragments of the present invention are to be inserted into one or more vectors, fragments may be ligated to produce repeats which can be separated by restriction sites. One or more of these repeats may be subsequently separated by cleavage with one or more restriction enzymes such as a blunt-end and/or sticky-end restriction endonuclease. A restriction endonuclease is an enzyme that has the capacity to recognize a specific base sequence (usually 4, 5, 6 base pairs in length or larger) in a DNA molecule, and to cleave the DNA molecule where this sequence appears. In the practice of the present invention, restriction enzymes and restriction sites can be chosen which give the same or different blunt-end or sticky-end fragments. Examples of blunt-end restriction enzymes suitable for use in the invention, and their cleavage sites, include without limitation:

AluI, DraI, Eco47 III, EcoRV, FspI, HpaI, MscI, NruI, PvuII, RsaI, ScaI, SmaI, SspI, StuI, ThaI, DraI

Examples of sticky-end restriction enzymes suitable for use in the invention, and their cleavage sites, include without limitation:

AvaI, BamHI, BanII, BglII, ClaI, EcoRI, HindIII, HpaII, KpnI, MseI, NcoI, NdeI, NotI, PstI, PvuI, SacI/SstI, XbaI, XhoI.

The above-mentioned restriction enzymes, and others that may be equivalently used in the present invention, are available commercially, for example from Life Technologies, Inc. (Rockville, Md.). See also Roberts, R. J., *Nucl. Acids Res.* 17(Suppl.):r347-r387 (1989), for other examples of restriction enzymes and their cleavage sites.

Preferably, the nucleic acid molecules used for making fragments of the ladders or compositions contains an origin of replication (for example, ori) such that the nucleic acid molecule may autonomously replicate within a host cell. It is also preferable that the nucleic acid molecule contain a selectable or screenable marker. The origin of replication and the marker may be present on the same fragment. Host cells containing the nucleic acid molecule of the invention may be cultured and selected with a selection agent corresponding to the selectable marker. Prokaryotic (gram negative or gram positive) or eukaryotic host cells may be used in accordance with the invention. Preferred prokaryotic host cells include bacteria of the genus *Escherchia, Salmonella, Pseudomonas* or *Klebsiella*. Preferably, *E. coli* strains are used (for example *E. coli* STBL2™ obtainable from Life Technologies, Inc. Rockville, Md.). Preferred eukaryotic host include yeast, plant cells, mammalian cells or insect cells.

According to the invention, the fragment sequences may be ligated into a vector which is then transformed into a host cell, using well known techniques. These multiple copies may be ligated together to form multimers, e.g. dimers, trimers, tetramers, pentamers, hexamers and the like. The host cell is then cultured, lysed, and the vector isolated by standard protocols. Please see e.g., Maniatis, Fitsch and Sambrook, *Molecular Cloning; A Laboratory Manual* (1982) or *DNA Cloning*, Volumes I and II (D. N. Glover ed. 1985) for general cloning methods. The vector may then be digested at the restriction endonuclease site, thereby separating the repeats to give multiple copies of the repeat fragment. Alternatively, partial digestion of the vector provides for multimers of varying sizes. Partial digest conditions which produce the desired multimers can be determined by standard methods such as visualizing the products of partial digests incubated for varying duration. Such multimers of variable size (e.g., monomers, dimers, trimers, etc.) are used as sizing ladders according to the invention and form "rungs" of the ladder. Such sizing ladders may be double-stranded or single-stranded. Single-stranded ladders may be formed from double-stranded nucleic acid molecules or ladders of the invention by techniques that are well-known to one of ordinary skill in the art.

According to the invention, nucleotides or derivatives thereof suitable for preparing the oligonucleotides and nucleic acid molecules of the invention include, but are not limited to, dUTP, dATP, dTTP, dCTP, dITP, ATP, TTP, UTP, GTP, CTP, 7-deaza-dGTP, adATP, adTTP, adGTP, adCTP, ddATP, ddTTP, ddCTP, and ddGTP. Other nucleotides (deoxy and dideoxy) and derivatives thereof suitable for use in forming the nucleic acid molecules of the invention will be familiar to one of ordinary skill in the art.

As described in more detail in Example 2 below, a preferred nucleic acid ladder may be produced from the plasmid pKB1847 (FIG. 1) by first digesting the plasmid to completion with BglII restriction enzyme to generate multiple copies of 100 bp, 200 bp, 300 bp, 400 bp, and 500 bp fragments as well as a 650 bp, 850 bp, and 1650 bp fragments and a 12 kb repeat "cassette" containing 12 1-kb repeats (see FIG. 1). The cassette is then partially digested with BamHI to generate fragments increasing in size by increments of 1 kb, the largest fragment being 12 kb. Of course, the steps of complete digestion and partial digestion may be reversed in sequence.

In accordance with the invention, the ladders or compositions may contain one or more highlight bands or fragments for orientation purposes. Such highlighted bands or fragments will have substantially more relative mass (greater than 3 times, preferably greater than 4 times, and most preferably greater than 5 times) than the other fragments or bands. Thus, the highlight fragments have brightened intensity upon staining so as to distinguish the highlight bands or fragments from other bands or fragments within the ladder or composition of the invention.

The sizing ladder or composition of the present invention can be used for estimating the size (in bp) of double-stranded nucleic acid (e.g. DNA or RNA) fragments, preferably by electrophoresis on agarose or polyacrylamide gels. This ladder may also be used to size single-stranded nucleic acid fragments when the strands are separated by heat or chemical denaturation. In particular, the ladder or composition of the present invention is useful as a standard for sizing linear, double-stranded and single-stranded nucleic acid fragments in the 25 kb to 10 bp range. The ladder or composition of the present invention can also be detectably labeled, for example with a radiolabel, fluorescent label, or chemiluminescent label as described below, and used as a standard in nucleic acid assays such as Southern hybridization, or PCR amplification wherein the size of the expected bands is within the range of the sizing ladder used.

The nucleic acid marker ladder or composition of the present invention may be single-stranded or double-stranded. The double-stranded ladder or composition is obtained directly from the double-stranded nucleic acid construct of the invention. Single strands may be obtained by heating the double-stranded nucleic acid construct of the invention, or by treating it with a chaotropic agent or with a helicase. Alternatively, single strands will be obtained when separating the ladder or composition on SDS-PAGE.

The ladder or composition of the invention can be detectably labeled by staining with ethidium bromide or SYBR green ([2-[N-(3-dimethylaminopropyl)-N-propylamino]-4-[2,3-dihydro-3-methyl-(benzo-1,3-thiazol-2-yl)-methylidene]-1-phenyl-quinolinium]+), or by end-labeling using standard methods known in the art. A particular advantage of the double stranded ladder or composition (e.g., DNA) of the present invention is the presence of a sticky end which comprises all four nucleotides as a result of the restriction digest, allowing use of any labeled nucleotide, A, C, T, G, for the purpose of detectably labeling the ladder or composition bands. Thus, another aspect of the invention relates to the ladder or composition of the present invention which is detectably labeled with a stain or other detectable label. Labels suitable for detectably labeling the ladder or composition of the invention include, but are not limited to, radiolabels (e.g., $^{32}$P, $^{14}$C, $^{3}$H and the like), fluorescent labels (e.g., fluorescein, rhodamine, phycocyanin, and the like) and chemiluminescent labels (e.g., using the PHOTO-GENE or ACES chemiluminescence systems, available commercially from Life Technologies, Inc. Rockville, Md.).

In another embodiment, the present invention relates to a nucleic acid marker kit comprising a carrier means such as a box or carton having in close confinement therein at least one container means such as vials, tubes, jars, ampules and the like. Such a kit may comprise the nucleic acid composition or ladder of the present invention, in optionally labeled form. The fragments of the ladder composition can be provided in separate containers or in premixed form. The ladders or composition or fragments thereof may be provided in a storage buffer such as about 10 mM TRIS-HCl (pH 8.0), about 1 mM EDTA and, optionally, about 50 mM NaCl. The nucleic acid ladder or composition may be present at a concentration of about 1 uM, and is preferably stored at about −20° C. until use. A further container means may contain a reagent capable of detectably labeling the ladder of the present invention, such as ethidium bromide, SYBR Green, or T4 polynucleotide kinase. Optionally, the ladder may be in a storage buffer containing glycerol, or sucrose, or a dye such as bromophenol blue or Xylene cyanol.

Having now generally described the invention, the same will be more readily understood through reference to the following Examples which are provided by way of illustration, and are not intended to be limiting of the present invention, unless specified.

The following MATERIALS AND METHODS were used in the examples that follow.

EXAMPLE 1

Production of the "pKB1847" Plasmid

Step 1:

A DNA ladder or composition according to the present invention is produced from a specially constructed plasmid ("pKB1847") designed to contain 9 copies of a 100 bp sequence, 4 copies of a 200 bp sequence, 3 copies of a 300 bp sequence, 2 copies of a 400 bp sequence, 2 copies of a 500 bp sequence, one copy each of a 650 bp, a 850 bp, and a 1650 bp sequence, and 12 copies of a 1000 bp sequence. The various size fragments are present in multiple copies in the plasmid to make the relative mass of each fragment proportional. The map of the plasmid is attached and was constructed by the following steps: A plasmid was designed to contain the pUC19 origin of replication and the ampicillin resistance gene in a fragment of an exact size of 1650 bp. A fragment containing the amplicillin gene (036 bp) and a fragment containing the origin of relocation (694 bp) were prepared by PCR-amplification with specific primers containing restriction sites, followed by restriction digestion and ligation of the PCR products, then transformation of the ligation mixture into competent DH5α E. coli cells. The resulting plasmid was designated "pHB106".

Step 2:

Two 1000 bp fragments were then PCR amplified from Lambda DNA to contain restriction enzyme sites such that when digested with these enzymes, they could be ligated together and cloned into the "pHB106" vector between EcoRI and HindIII restriction sites.

Step 3:

The resulting plasmid contained an asymmetrical AvaI site (CTCGGG) between the two 1 Kb fragments which was then used to ligate in other 1 Kb fragments which were flanked by the same asymmetrical AvaI site. This ensured that the 1 Kb fragments ligated into the plasmid in a head-to-tail fashion. A plasmid was isolated which contains twelve 1 Kb fragments ("pKB1603").

Step 4:

A 100 bp fragment was amplified from Lambda DNA and multiple copies were cloned into the EcoRI site of pHB106 as described in Steps 2 and 3. A plasmid was isolated which contains nine 100 bp fragments ("pKB1213").

Step 5:

The procedure described in Step 4 was repeated to clone four 200 bp fragments ("pKB2110"), three 300 bp fragments ("pKB3106"), two 400 bp fragments ("pKB4103"), and two 500 bp fragments ("pKB5006") into pHB106 vectors.

Step 6:

The plasmid pKB3106, containing the multimers of the 300 bp fragment, and the plasmid pKB4103, containing the multimers of the 400 bp fragment, were both digested at two restriction sites and fragments from each plasmid were gel-purified and ligated together. A new plasmid was formed containing the 300 bp multimers and the 400 bp multimers head-to-tail.

Step 7:

The 100 bp, 200 bp and 500 bp multimers were then cloned into the plasmid containing the 300 and 400 bp multimers using three more "cycles" of the method described in Step 6. The resulting plasmid contained all of the multimers of the 100, 200, 300, 400, and 500 bp fragments.

Step 8:

The "cassette" containing the multimers of the 100 bp through 500 bp fragments was cut out of the plasmid from step 7 and ligated into the plasmid, pKB1603, described in step 3 which contains the twelve 1000 bp fragments.

Step 9:

A 650 bp fragment and a 850 bp fragment, both generated by PCR from Lambda DNA, were cloned into unique restriction enzyme sites in the plasmid described in Step 8. The resulting plasmid was designated, "pKB1847". This plasmid contained in E. coli STBL2™ cells, was deposited on Jun. 20, 1997 with The Collection, Agricultural Research Culture Collection (NRRL), 1815 North University Street, Peoria, Ill. 61604 USA as Deposit No. NRRL B-21791.

EXAMPLE 2

Production of the DNA Ladder

The DNA Ladder is produced from the plasmid pKB1847 by first digesting the plasmid to completion with BglII restriction enzyme. This releases the multiple copies of the 100 bp, 200 bp, 300 bp, 400 bp, and 500 bp fragments as well as the 650 bp, 850 bp and 1650 bp fragments and the 12 Kb repeat fragment. This mixture is then partially digested with BamHI restriction enzyme to generate fragments increasing in size by 1 Kb, the largest fragment being 12 Kb (see Table 1). The BamHI and BglII restriction enzymes both generate identical "sticky ends" in each fragment of the ladder with the sequence, GATC.

TABLE 1

DNA Ladder of the present invention - Relative Mass of Ladder Bands

| Ladder Band Size (bp) | Number of Fragments in Plasmid | Mass (bp) (# of Fragments × size) | Relative Mass [(mass/(total plasmid size) × 100%] |
|---|---|---|---|
| 12,000 | | | *5.1% |
| 11,000 | | | *5.1% |
| 10,000 | | | *5.1% |
| 9,000 | | | *5.1% |
| 8,000 | | | *5.1% |
| 7,000 | | | *5.1% |
| 6,000 | | | *5.1% |
| 5,000 | | | *5.1% |
| 4,000 | | | *5.1% |
| 3,000 | | | *5.1% |
| 2,000 | | | *5.1% |
| 1,650 | 1 | 1,650 | 8.4% |
| 1,000 | 12* | 12,000* | *5.1% |
| 850 | 1 | 850 | 4.3% |
| 650 | 1 | 650 | 3.3% |
| 500 | 2 | 1,000 | 5.1% |
| 400 | 2 | 800 | 4.1% |
| 300 | 3 | 900 | 4.6% |
| 200 | 4 | 800 | 4.1% |
| 100 | 9 | 900 | 4.6% |

Total plasmid size = 19,550 bp
*= The 12,000 bp mass comprises 12 separate bands.

EXAMPLE 3

Gel Electrophoresis and Ethidium Bromide Staining

Material was obtained from eight companies with comparable nucleic acid ladder products and analyzed simultaneously with the DNA Ladder or composition of the invention as follows:

250 ng of DNA were applied to the wells of a 1% agarose gel which contained 1 ug/ml of ethidium bromide. The gel was submerged in Tris-Acetate-EDTA buffer, also containing 1 ug/ml of ethidium bromide, in an electrophoresis apparatus. The gel was electrophoresed at 100 V for 40 minutes. The bands were analyzed by photographing the gel under exposure of UV light.

Figure 2:
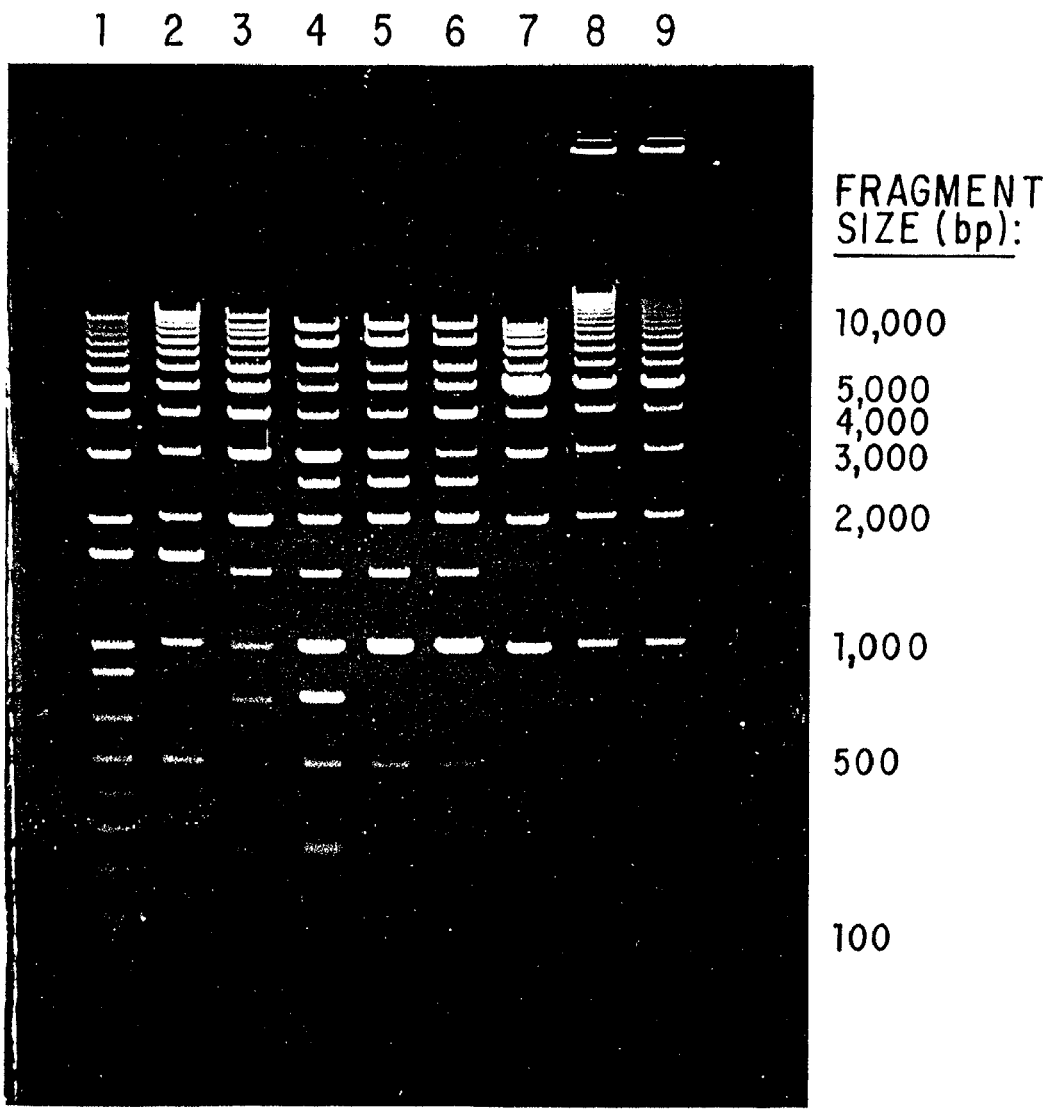
FIG. 2 is a photograph of a comparative gel illustrating the distinguishing features of the present invention compared to existing DNA standards.

FIG. 2 is a photograph of the gel illustrating the intensity and number of DNA bands in the various ladders. The following describes the differences between the invention and the commercially available related products when analyzed by gel electrophoresis:

The product of the invention is illustrated in FIG. 2, Lane 1. Significantly, all of the ladder bands, especially the bands smaller than 1 kb in length, stain with relative equal intensity with ethidium bromide since the mass of DNA in each of the bands is relatively proportional.

As can be seen in FIG. 2, Lane 2, the 1 Kb DNA Ladder commercially available from Life Technologies, Inc. (Rockville, Md.) differs from the invention in that the fragments smaller than 1 Kb appear less intense than the 1018 bp increment bands. This is because the relative mass of each of these fragments (and thus the intensity of these bands when stained) decreases in proportion to its size. Also, the 1,636 bp band and the 500 bp band stain more intensely than do other bands in the ladder.

Lane 3 illustrates the "Kb DNA Ladder" from Stratagene (La Jolla, Calif.). The intensity of the bands smaller than 2 Kb is about half that of the bands 2 Kb and larger. This feature is described as a landmark for reference purposes. In addition, the ladder bands greater than 6 Kb stain with less intensity than the 2 Kb-6 Kb bands.

The 1 Kb and 3 Kb bands in the 1 Kb DNA Ladder available from Promega (Madison, Wis.) (Lane 4) have increased intensity (>2-fold) to serve as reference points within the ladder. In addition to this, the 8 Kb and 10 Kb bands are significantly more intense than other bands in the ladder and the 0.25, 0.5, and 0.75 Kb bands are of various intensities.

Several of the bands in the 1 Kb DNA Ladder sold by Sigma (St. Louis, Mo.) (see Lane 5) vary in their intensities and this ladder contains only one band smaller than 1 Kb.

The 1 Kb DNA Ladder sold by Pharmacia (Piscataway, N.J.) (Lane 6) is identical to the Sigma ladder, and is likely the same product.

The Bayou Biolabs (Harahan, La.) product in Lane 7 has a triple-intense 5 Kb band and does not contain any bands smaller than 1 Kb.

The two 1 Kb DNA Ladders in Lanes 8 and 9 (GenSura (DelMar, Calif.) and Invitrogen (San Diego, Calif.)) are identical products which have 5 Kb bands of higher intensity and no bands smaller than 1 Kb.

What is claimed is:

1. A nucleic acid ladder consisting essentially of a plurality of double stranded nucleic acid fragments, each fragment having a size in base pairs of between 20 kb and 100 base pairs, a copy number, a mass, and a relative mass wherein the mass of each fragment is the size in base pairs of the fragment multiplied by the copy number of the fragment, wherein the relative mass of each fragment is the mass of the fragment divided by the sum of the masses of all of the fragments, wherein the relative mass of any one fragment of the plurality is no more than 3 time the relative mass of any other fragment of the plurality, wherein at least two of the plurality of nucleic acid fragments have a size greater than 1 kb, and wherein at least two of the plurality of nucleic acid fragments have a size less than 1 kb, wherein the nucleic acid ladder lacks a highlight fragment.

2. The nucleic acid ladder of claim 1, wherein at least 3 of the plurality of double stranded nucleic acid fragments have a size greater than 1 kb, and wherein at least 3 of the double stranded nucleic acid fragments have a size less than 1 kb.

3. The nucleic acid ladder of claim 1, wherein at least 4 of the plurality of double stranded nucleic acid fragments have a size greater than 1 kb, and wherein at least 4 of the plurality of double stranded nucleic acid fragments have a size less than 1 kb.

4. The nucleic acid ladder of claim 1, wherein at least 5 of the plurality of double stranded nucleic acid fragments have a size greater than 1 kb, and wherein at least 5 of the plurality of double stranded nucleic acid fragments have a size less than 1 kb.

5. The nucleic acid ladder of claim 1, wherein the plurality of double stranded nucleic acid fragments are stained with a detectable label.

6. The nucleic acid ladder of claim 5, wherein the detectable label is [2-[N-(3-dimethylaminopropyl)-N-propylamino]-4-[2,3-dihydro-3-methyl-(benzo-1,3-thiazol-2-yl)-methylidene]-1-phenyl-quinolinium]+.

7. The nucleic acid ladder of claim 5, wherein the detectable label is ethidium bromide.

8. The nucleic acid ladder of claim 1, wherein the relative mass of any one fragment of the plurality is no more than 2.5 times the relative mass of any other fragment of the plurality.

9. The nucleic acid ladder of claim 1, wherein the relative mass of any one fragment of the plurality is no more than 2 times the relative mass of any other fragment of the plurality.

10. The nucleic acid ladder of claim 1, wherein the relative mass of any one fragment of the plurality is no more than 1.5 times the relative mass of any other fragment of the plurality.

11. A nucleic acid ladder comprising a plurality of double stranded nucleic acid fragments, wherein three or more of the fragments are of a size selected from the group consisting of:
   (a) 100 base pairs,
   (b) 200 base pairs,
   (c) 300 base pairs,
   (d) 400 base pairs,
   (e) 500 base pairs,
   (f) 650 base pairs,
   (g) 850 base pairs, and
   (h) 1650 base pairs; and
wherein two or more of the fragments are of a size selected from the group consisting of:
   (a) 1 kilobase pairs,
   (b) 2 kilobase pairs,
   (c) 3 kilobase pairs,
   (d) 4 kilobase pairs, and
   (e) 5 kilobase pairs;
   wherein each fragment has a copy number, a mass, and a relative mass wherein the mass of each fragment is the size in base pairs of the fragment multiplied by the copy number of the fragment, wherein the relative mass of each fragment is the mass of the fragment divided by the sum of the masses of all of the fragments, wherein the relative mass of any one fragment of the plurality is no more than 3 time the relative mass of any other fragment of the plurality.

12. The nucleic acid ladder of claim 11, wherein four or more of the fragments are between 100 base pairs and 1650 base pairs.

13. The nucleic acid ladder of claim 12, wherein five or more of the fragments are between 100 base pairs and 1650 base pairs.

14. The nucleic acid ladder of claim 12, wherein three or more of the fragments are between 1 kilobase pairs and 5 kilobase pairs.

15. A nucleic acid ladder comprising a plurality of double stranded nucleic acid fragments, wherein three or more of the fragments are of a size selected from the group consisting of:
(a) 100 base pairs,
(b) 200 base pairs,
(c) 300 base pairs,
(d) 400 base pairs,
(e) 500 base pairs,
(f) 650 base pairs,
(g) 850 base pairs, and
(h) 1650 base pairs; and
wherein two or more of the fragments are of a size selected from the group consisting of:
(a) 1 kilobase pairs,
(b) 2 kilobase pairs,
(c) 3 kilobase pairs,
(d) 4 kilobase pairs, and
(e) 5 kilobase pairs;
wherein each fragment has a copy number, a mass, and a relative mass wherein the mass of each fragment is the size in base pairs of the fragment multiplied by the copy number of the fragment, wherein the relative mass of each fragment is the mass of the fragment divided by the sum of the masses of all of the fragments, wherein the relative mass of any one fragment of the plurality is no more than 3 time the relative mass of any other fragment of the plurality and
wherein the nucleic acid ladder further comprises at least one highlight fragment having a size in the range of 100 base pairs to 5 kilobase pairs and having a relative mass that is three times greater than the relative mass of other molecules in the composition.

16. The nucleic acid ladder of claim 15, wherein four or more of the fragments are between 100 base pairs and 1650 base pairs.

17. The nucleic acid ladder of claim 15, wherein five or more of the fragments are between 100 base pairs and 1650 base pairs.

18. The nucleic acid ladder of claim 15, wherein three or more of the fragments are between 1 kilobase pairs and 5 kilobase pairs.

19. The nucleic acid ladder of claim 15, wherein the highlight fragment has a relative mass that is at least 5 times greater than the other fragments.

* * * * *